United States Patent
Wang et al.

(10) Patent No.: US 10,172,962 B2
(45) Date of Patent: Jan. 8, 2019

(54) MACROMOLECULAR DELIVERY SYSTEMS FOR NON-INVASIVE IMAGING, EVALUATION AND TREATMENT OF ARTHRITIS AND OTHER INFLAMMATORY DISEASES

(71) Applicant: University of Utah Research Foundation, Salt Lake City, UT (US)

(72) Inventors: Dong Wang, Omaha, NE (US); Jindrich Kopecek, Salt Lake City, UT (US); Scott C. Miller, Salt Lake City, UT (US); Pavla Kopeckova, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/875,015

(22) Filed: Jan. 19, 2018

(65) Prior Publication Data

US 2018/0207296 A1    Jul. 26, 2018

Related U.S. Application Data

(62) Division of application No. 10/591,258, filed as application No. PCT/US2005/010801 on Mar. 30, 2005.

(Continued)

(51) Int. Cl.
*A61K 9/14* (2006.01)
*A61K 49/00* (2006.01)
(Continued)

(52) U.S. Cl.
CPC .......... *A61K 49/0054* (2013.01); *A61K 47/58* (2017.08); *A61K 49/0041* (2013.01); *A61K 49/128* (2013.01)

(58) Field of Classification Search
None
See application file for complete search history.

(56) References Cited

U.S. PATENT DOCUMENTS 5,037,883 A * 8/1991 Kopecek ............ A61K 47/6883
                                                     525/54.1
5,258,453 A * 11/1993 Kopecek .......... A61K 47/48176
                                                     424/78.17

(Continued)

FOREIGN PATENT DOCUMENTS

EP       0331471 A1    3/1989
WO    2004/002528 A1   1/2004

(Continued)

OTHER PUBLICATIONS

Etrych et al.; "New HPMA copolymers containing doxorubicin bound via pH-sensitive linkage: synthesis and preliminary in vitro and in vivo biological properties," 2001, Elsevier, Journal of Controlled Release, vol. 73, pp. 89-102.*

(Continued)

*Primary Examiner* — Devang K Thakor
*Assistant Examiner* — Ivan A Greene
(74) *Attorney, Agent, or Firm* — Robert C. Netter, Jr.; Dann, Dorfman, Herrell & Skillman

(57) ABSTRACT

This invention relates to biotechnology, more particularly, to water-soluble polymeric delivery systems for the imaging, evaluation and/or treatment of rheumatoid arthritis and other inflammatory diseases. Using modern MR imaging techniques, the specific accumulation of macromolecules in arthritic joints in adjuvant-induced arthritis in rats is demonstrated. The strong correlation between the uptake and retention of the MR contrast agent labeled polymer with histopathological features of inflammation and local tissue (Continued)

damage demonstrates the practical applications of the macromolecular delivery system of the invention.

11 Claims, 10 Drawing Sheets

Related U.S. Application Data

(60) Provisional application No. 60/558,047, filed on Mar. 31, 2004.

(51) Int. Cl.
*A61K 49/12* (2006.01)
*A61K 47/58* (2017.01)

(56) References Cited

U.S. PATENT DOCUMENTS

| | | | |
|---|---|---|---|
| 5,356,633 A | 10/1994 | Woodle et al. | |
| 6,436,386 B1 | 8/2002 | Roberts et al. | |
| 6,528,097 B1 | 3/2003 | Vaugh et al. | |
| 2004/0043030 A1* | 3/2004 | Griffiths | A61K 51/088 424/178.1 |
| 2006/0127310 A1 | 6/2006 | Russell-Jones et al. | |

FOREIGN PATENT DOCUMENTS

| | | |
|---|---|---|
| WO | 2004/045647 A1 | 6/2004 |
| WO | 2005/097073 A1 | 10/2005 |

OTHER PUBLICATIONS

Timofeevski et al.; "Anti-inflammatory and Antishock Water-soluble Polyesters of Glucocorticoids with Low Level Systemic Toxicity," 1996, PLENUM, Pharmaceutical Research, vol. 13, No. 3, pp. 476-480.*
Quan et al. "Development of a macromolecular prodrug for the treatment of inflammatory arthritis: mechanisms involved in arthrotropism and sustained therapeutic efficacy," BioMed Central, Arthritis Research & Therapy, (2010)12:R170, pp. 1-10.*
Wang, Dong et al.; "Novel dexamethasone-HPMA copolymer conjugate and its potential application in treatment of rheumatoid arthritis," BioMed Central, Arthritis Research & Therapy, (2007)9:R2, pp. 1-9.*
Ren, K., et al., "Macromolecular prodrug of dexamethasone prevents particle-induced pen-implant osteolysis with reduced systemic side effects" J. Control Release (2014) 175:1-9.
Yuan, F., et al., "Dexamethasone Prodrug Treatment Prevents Nephritis in Lupusprone (NZB×NZW)F1 Mice without Causing Systemic Side Effects" Arthritis Rheum. (2012) 64(12):4029-4039.
Liu, X-M. et al., "Synthesis and Evaluation of a Well-defined HPMA Copolymer-Dexamethasone Conjugate for Effective Treatment of Rheumatoid Arthritis" Pharm. Res. (2008) 25(12):2910-2919.
Metselaar, J.M., et al. "Complete remission of experimental arthritis by joint targeting of glucocorticoids with long-circulating liposomes" Arthritis Rheum. (2003) 48(7):2059-66.
Timofeevski, S.L., et al. "Anti-inflammatory and antishock water-soluble polyesters of glucocorticoids with low level systemic toxicity" Pharm. Res. (1996) 13(3):476-80.
Kakimoto, K., et al. "The suppressive effect of gelatin-conjugated superoxide dismutase on disease development and severity of collagen-induced arthritis in mice" Clin. Exp. Immunol. (1993) 94(2):241-6.
Wang, D., et al. "Inhibition of cathepsin K with lysosomotropic macromolecular inhibitors" Biochemistry (2002) 41(28):8849-59.
Gupta, H., et al. "Inflammation: imaging with methoxy poly(ethylene glycol)-poly-L-lysine-DTPA, a long-circulating graft copolymer" Radiology (1995) 197(3):665-9.
Wang, D., et al. "Synthesis and evaluation of water-soluble polymeric bone-targeted drug delivery systems" Bioconjug. Chem. (2003) 14(5):853-9.
Wang, L.F., et al. "pH sensitive polymeric prodrugs containing ibprofen, ketoprofen and naproxen as pendent groups." Journal of Bioactive and Compatible Polymers. (1999) 14(5):415-428.
Omelyanenko, V., et al., "Targetable HPMA copolymer-adriamycin conjugates. Recognition, internalization, and subcelular fate" J. Controlled Rel. (1998) 53:25-37.
Smolen, J.S., et al., "Therapeutic Strategies for Rheumatoid Arthritis" Nat. Rev. (2003) 2:473-488.
Etrych, T., et al., "New HPMA copolymers containing doxorubicin bound via pH-sensitive linkage: synthesis and preliminary in vitro and in vivo biological properties" J. Controlled Rel. (2001) 73(1):89-102.
Lewis, R.J., "Hawley's Condensed Chemical Dictionary" 15th Ed. (2007) Wiley—Interscience; p. 1013, entry for "polymer".
Merriam-Webster's Collegiate Dictionary, 11th Ed., Merriam-Webster, Inc., Springfield, Massachusetts (2004) p. 336, entry for "derivative".
PCT International Search Report, PCT/US2005/010801, dated Jul. 20, 2005.
PCT Written Opinion, PCT/US2015/010801, dated Jul. 20, 2005.
Falchuk, K.H., et al., "Respiratory gases of synovial fluids. An approach to synovial tissue circulatory-metabolic imbalance in rheumatoid arthritis" Am. J. Med. (1970) 49(2):223-31.
Kopecek, Jindrich, "Synthesis of Tailor-Made Soluble Polymeric Drug Carriers" (1084) Plenum Press; Recent Advances in Drtug Delivery Systems, James M Anderson & Sung Wan Kim, Eds.; pp. 41-62.

* cited by examiner

FIG. 5

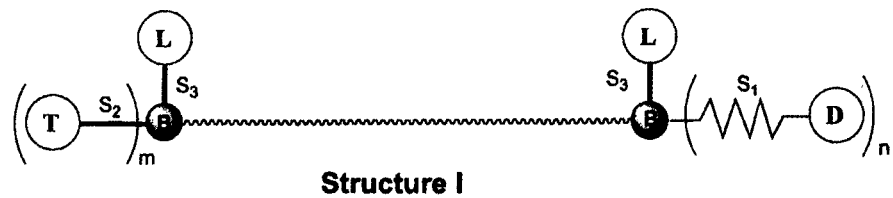

Structure I

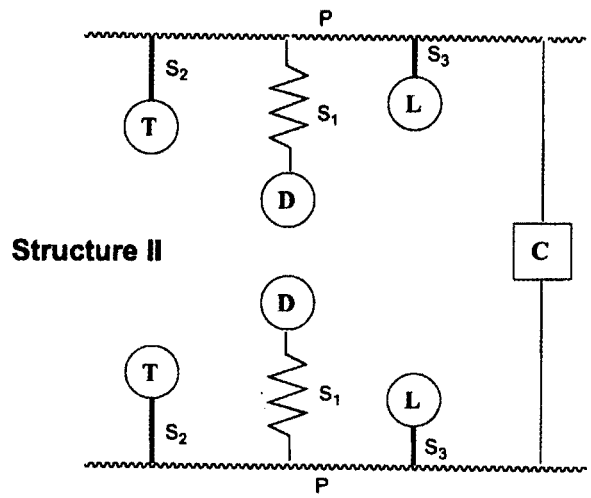

Structure II

(T) Targeting moieties covalently bonded to the polymer terminus or backbone via spacer $S_2$ ———

(D) Anti-inflammatory drugs or non-invasive imaging agentss or mixture of both, bonded to the polymer via spacer $S_1$ —/\/\/\—

(L) Optional bio-assay label covalently bonded to the polymer backbone via non-degradable spacer $S_3$ ———

(B) Branching structure.

———[C]——— Optional biodegradable cross-linkage in the delivery system

∿∿∿∿∿∿∿∿ Inert polymeric backbone of the delivery system, P

MACROMOLECULAR DELIVERY SYSTEMS FOR NON-INVASIVE IMAGING, EVALUATION AND TREATMENT OF ARTHRITIS AND OTHER INFLAMMATORY DISEASES

PRIORITY CLAIM

This application is a divisional of U.S. Patent Application Ser. No. 10/591,258, filed on Nov. 28, 2006, which is a § 371 application of PCT/US2005/010801, filed Mar. 30, 2005, which in turn claims the benefit of U.S. Provisional Patent Application No. 60/558,047, filed on Mar. 31, 2004. The foregoing applications are incorporated by reference herein.

STATEMENT REGARDING FEDERALLY SPONSORED RESEARCH OR DEVELOPMENT

Work described herein was supported in part by National Institute of Health Grant No. EB00251. The United States Government may have certain rights in the invention.

TECHNICAL FIELD

This invention relates to biotechnology, more particularly, to water-soluble polymeric delivery systems for non-invasive imaging, evaluation and treatment of arthritis and other inflammatory diseases.

BACKGROUND

Rheumatoid arthritis (RA) is the most common inflammatory arthritis, affecting about 1 percent of the general population worldwide. In United States, about 4.5% of people over the age of 55 people have been affected (1, 2).

As a symmetric disease, RA usually involves the same joints on both sides of the body. Angiogenesis and microvascular lesions are common features of RA inflammation, which leads to abnormal serum protein infiltration into the synovia (3-5). Damaged or depleted lymphatics have been observed in the synovium of RA patients as well (6, 7).

Although the exact cause of rheumatoid arthritis is unknown, many medications have been developed to relieve its symptoms and slow or halt its progression. Most commonly used medications rest on three principal approaches: symptomatic treatment with non-steroidal anti-inflammatory drugs (NSAIDs), corticosteroid and disease-modifying antirheumatic drugs (DMARDs) (3).

Considerable effort has been made to identify and develop new therapeutic strategies for the treatment of RA. RA medications, such as cycloxygenase-2 (COX-2) specific inhibitor (a NSAID) (8), tumor necrosis factor (TNF) blockers and interleukin-1 receptor antagonists (IL-1Ra) (DMARDs) have been used for clinical applications (3). Although the new generation of antirheumatic drugs have higher specificity to their molecular target, most of them do not have specificity to the diseased tissue, which lead to various side effects that limit their clinical application. Well-known side effects of NSAIDs include indigestion, stomach bleeding, liver and kidney damage, ringing in ears (tinnitus), fluid retention, and high blood pressure (9). Well known side effects of corticosteroids include bruising, thinning of bones, cataracts, weight gain, redistribution of fat, diabetes and high blood pressure (10). Some DMARDs are immunosuppressants and usually lead to serious side effects, such as increased susceptibility to infection (3). The recent withdrawal of Vioxx® (COX-2 inhibitor, Merck) is a good example of the tremendous impact that side effects can have on an otherwise effective drug.

The ubiquitous in vivo distribution of receptors utilized by most of the antirheumatic drugs is a leading cause of their side effects. Therapeutic delivery systems, which could specifically deliver anti-arthritis drugs to the diseased tissue of RA patients, may avoid many of the side effects that are manifested in other tissues while achieving much greater clinical therapeutic efficacy.

The application of water-soluble polymers as a drug carrier for effective delivery of the drug to the desired sites (macromolecular therapy) has been extensively studied for the past two decades in the treatment of solid tumors (11). Because of the "leaky" vasculature and poorly developed lymphatic system, extravasated macromolecules can be efficiently accumulated in the solid tumor. This phenomenon is termed tumor-selective "enhanced permeability and retention" (EPR) and has been used successfully to target anticancer drugs to solid tumors (12).

Studies using micro-particular carriers, such as liposomes for the delivery of anti-arthritic agents to a RA joint indicate some promising results in an animal model of arthritis (13). But the hepatotropism of the liposome may be problematic due to secondary livery toxicity. Therefore, there exists a need in the art for an effective drug delivery system that targets the appropriate tissues.

DISCLOSURE OF THE INVENTION

The invention relates to water-soluble polymeric delivery systems. In one embodiment, the delivery system is used for delivery of drugs to the diseased sites for the treatment of rheumatoid arthritis and other inflammatory diseases. In another embodiment, the delivery system is used for delivery of imaging agents to the diseased sites for non-invasive imaging and evaluation of the diseased sites of arthritis and other inflammatory diseases.

In an exemplary embodiment, the invention provides water-soluble delivery systems for the delivery of anti-inflammatory therapeutic agents selected from the group consisting of proteins, peptides, NSAIDs, DMARDs, glucocorticoids, methotrexate, sulfasalazine, chloriquine, gold, gold salt, copper, copper salt, penicillamine, D-penicillamine, cyclosporine, etc. and mixtures thereof, such drugs are well-known to those of skill in the art (37, 38).

In another exemplary embodiment, the invention provides a water-soluble polymeric delivery system for delivery of imaging agents, which are useful for non-invasive imaging and evaluation of arthritic joints and other inflammatory diseased organs or tissues. The imaging agents may be selected from any of the known compounds, for example, compounds useful for MRI, PET, CT or γ-scintigraphy imaging, etc. and mixtures thereof, such agents are well-known to those of skill in the art.

In another exemplary embodiment, the invention provides a water-soluble polymeric delivery system for delivery of a combination of imaging agents and anti-inflammatory therapeutic agents. In another exemplary embodiment, the invention provides a method of treating an inflammatory disease and monitoring the progress of the treatment. In another exemplary embodiment, the invention provides a method of screening anti-inflammatory therapeutic agents, wherein the anti-inflammatory agent is attached to a water-soluble polymeric delivery system of the invention and administered to a subject, the effect of the therapeutic agent is monitored, for example, using an imaging agent, and an effective therapeutic agent is identified. Optionally, an imaging agent may be co-administered for the purpose of monitoring and/or screening the activity of the anti-inflammatory agent. Optionally, a targeting moiety or moieties may be used in the method of screening.

In another exemplary embodiment, the inflammatory disease is rheumatoid arthritis, osteoarthritis, temprormandibular joint syndrome, inflamed nerve root, Crohn's disease, chronic obstructive pulmonary disease, psoriasis diseases, asthma, colitis, multiple sclerosis, lupus, erythematosus, atherosclerosis and/or the like.

In another exemplary embodiment, the invention relates to drug delivery systems comprising a water-soluble polymer backbone, optionally, a targeting moiety or moieties, and a therapeutic agent or agents, and/or an imaging agent. The linkage (or linkages) between the targeting moiety (or moieties) and the polymer backbone is non-degradable or degradable under physiological conditions. The linkage (or linkages) between the therapeutic agent (or agents) and the polymer backbone is non-degradable or degradable under physiological conditions.

In another exemplary embodiment, the invention relates to delivery systems for imaging agents comprising a water-soluble polymer backbone, optionally, a targeting moiety or moieties, and an imaging agent or agents. The linkage (or linkages) between the targeting moiety (or moieties) and the polymer backbone is non-degradable or degradable under physiological conditions. The linkage (or linkages) between the imaging agent (or agents) and the polymer backbone is non-degradable or degradable under physiological conditions.

In yet another exemplary embodiment, the invention provides a method of manufacturing a pharmaceutical composition and/or medicament comprising one or more delivery systems of the invention for the treatment of rheumatoid arthritis, osteoarthritis, temprormandibular joint syndrome, inflamed nerve root, Crohn's disease, chronic obstructive pulmonary disease, psoriasis diseases, asthma, colitis, multiple sclerosis, lupus, erythematosus, atherosclerosis and/or the like.

As will be apparent to a person of ordinary skill in the art based on the invention described herein, the invention provides the advantage of incorporating multiple therapeutic agents, targeting moieties, bio-assays labels, spacers and/or imaging agents, which may include a plurality of different chemical species from one or more of these groups. Therefore, in yet another exemplary embodiment the therapeutic agents, targeting moieties, bio-assays labels, spacers and/or imaging agents may consist of any number or combination of different species, having the same or different effects.

BRIEF DESCRIPTION OF THE DRAWINGS

FIG. 2A is a low power micrograph of the ankle and foot bones. Extensive swelling and inflammation is evident in the soft tissues (*) surrounding the foot bones. T=tibia. FIG. 2B shows the tarsal joint illustrating inflamed synovium (synovitis), extensive inflammatory infiltration (*) and cartilage and bone destruction. B=bone, A=articular cartilages. FIG. 2C is a higher power micrograph of the inflamed synovium. A=articular cartilage. FIG. 2D shows extensive bony destruction with inflammatory infiltration (*) in a tarsal (ankle) bone. Bone surfaces are lining with large active osteoclasts (arrows). FIG. 2E illustrates several blood vessels in an inflamed region of the ankle joint illustrating the inflammatory reaction around the vessels. The endothelial lining is thickened and vacuolated (arrows). FIG. 2F is a low power micrograph of the knee joint from this same animal. There joint is quite normal in appearance except for a small pocket of inflammation on the posterial aspect of the joint (arrow). This same area was contrasted when observed by MRI. T=tibia; F=femur.

FIG. 3A shows AIA rat baseline; FIG. 3B shows AIA rat, 5 minutes post injection of P-DOTA-$Gd^{3+}$; FIG. 3C shows AIA rat, 1 hour post injection of P-DOTA-$Gd^{3+}$; FIG. 3D shows AIA rat, 2 hours post injection of P-DOTA-$Gd^{3+}$; FIG. 3E shows AIA rat, 3 hours post injection of P-DOTA-$Gd^{3+}$; FIG. 3F shows AIA rat, 8 hours post injection of P-DOTA-$Gd^{3+}$; FIG. 3G shows AIA rat, 32 hours post injection of P-DOTA-$Gd^{3+}$; FIG. 3H shows AIA rat, 48 hours post injection of P-DOTA-$Gd^{3+}$; FIG. 3I. Healthy rat, baseline; FIG. 3J shows healthy rat, 5 minutes post injection of P-DOTA-$Gd^{3+}$; FIG. 3K. Healthy rat, 1 hour post injection of P-DOTA-$Gd^{3+}$; FIG. 3L shows healthy rat, 2 hours post injection of P-DOTA-$Gd^{3+}$; FIG. 3M. Healthy rat, 8 hours post injection of P-DOTA-$Gd^{3+}$; FIG. 3N shows healthy rat, 48 hours post injection of P-DOTA-$Gd^{3+}$; FIG. 3O shows AIA rat, 5 minutes post injection of OMNISCAN; FIG. 3P shows AIA rat, 2 hours post injection of OMNISCAN; FIG. 3Q shows AIA rat, 8 hours post injection of OMNISCAN; FIG. 3R shows AIA rat, 32 hours post injection of OMNISCAN; FIG. 3S shows AIA rat, 48 hours post injection of OMNISCAN; FIG. 3T shows healthy rat, 5 minutes post injection of OMNISCAN; FIG. 3U shows healthy rat, 1 hour post injection of OMNISCAN; FIG. 3V shows healthy rat, 2 hours post injection of OMNISCAN; FIG. 3W shows healthy rat, 8 hours post injection of OMNISCAN; FIG. 3X shows healthy rat, 48 hours post injection of OMNISCAN.

FIG. 4A shows baseline MR image of AIA rat; FIG. 4B shows an MR image of AIA rat's left ankle and paw, 2 hours post injection; FIG. 4C shows an MR image of AIA rat's left ankle and paw, 8 hours post injection; FIG. 4D shows an MR image of ALA rat's left knee joint, 8 hours post injection.

FIG. 5 illustrates the general structure of the water-soluble polymeric delivery system. The average mol percentage of targeting moieties (T) per polymer chain may range anywhere from 0% to about 50%, preferably from 0% to 30%; The average mol percentage of therapeutic agents or imaging agents (D) or mixture of both per polymer chain may range anywhere from 1% to about 90%; The average mol percentage of bio-assay label (L) per polymer chain may range anywhere from 0% to about 50%. The spacer $S_1$ and $S_2$ can be covalent or physical bonds or linkages, such as peptides or other complex chemical structures, which may or may not be cleaved upon stimulus, such as change of pH, specific enzyme activity (for example, cathepsin K, MMPs, etc.), presence or absence of oxygen, etc. under physiological condition. The spacer $S_3$ illustrates a non-degradable, under physiological condition, covalent or physical bond or linkage. The optional biodegradable cross-linkage (C) can be covalent or physical bonds or linkages, such as peptides or other complex chemical structures, which may be cleaved upon stimulus, such as a change of pH, specific enzyme activity (e.g., cathepsin K, MMPs, etc.), presence or absence of oxygen, etc., under physiological conditions.

BEST MODE(S) FOR CARRYING OUT THE INVENTION

Figure 1:
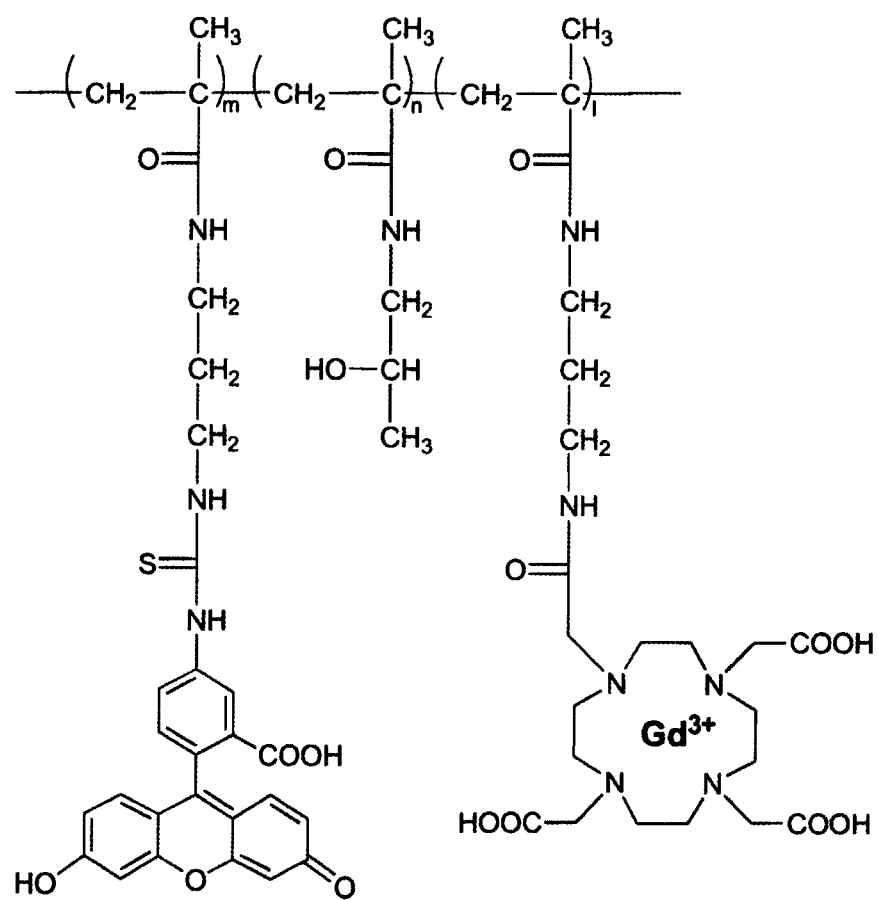
FIG. 1 illustrates the chemical structure of a exemplary polymeric delivery system for MRI contrast agent (DOTA-$Gd^{3+}$), abbreviated as P-DOTA-$Gd^{3+}$, for the imaging of arthritic joints and evaluation of the severity of the disease.

Throughout the description of the invention and the claims, and following convention, the "singular" includes the "plural"; for example, a therapeutic agent and/or a targeting moiety, means at least one such therapeutic agent or targeting moiety, unless indicated otherwise.

To demonstrate the principle of the invention, conventional visual examination with Evans blue dye (EB) injection and magnetic resonance imaging (MRI) techniques were used to follow the in vivo fate of macromolecules on an established AIA rat model. Additionally, histological examination confirmed the presence of disease in specific anatomical locations where the macromolecular delivery system is identified with MRI technique.

EB is a commonly used agent to assess vascular permeability and integrity (23). It is a dye-carrying multiple charges and aromatic structures, which forms a strong complex with plasma albumin. Injection of the dye had been successfully used to establish the concept of macromolecular therapy for the treatment of solid tumors (24). In this experiment, the EB dye technique was used in AIA rats to visually assess the accumulation of plasma albumin in inflamed joints. The hind paw of the AIA rats, where the most severe inflammation was evident, readily incorporated the dye compared with that observed in the healthy rats. This observation confirmed that there was indeed a much greater concentration of plasma albumin in the inflamed joints of the AIA rat model.

Although the results with EB are significant, it is noted that the dye is not covalently bound to albumin and some dye transfers nonspecifically to other tissues. For example, a slight blue staining was evident in some organs, including the liver and heart.

Magnetic resonance imaging (MM) is a noninvasive method of mapping the internal structure of the body. It employs radiofrequency (RF) radiation in the presence of carefully controlled magnetic fields in order to produce high quality cross-sectional images of the body in any plane. It portrays the distribution of hydrogen nuclei and parameters relating to their motion in water and lipids. Introduction of paramagnetic contrast agents would shorten $T_1$ (the longitudinal relaxation time) of the hydrogen nuclei in tissues, which in turn will increase the MR signal intensity thereof (14). Therefore, to further support the results, magnetic resonance imaging (MRI) was used to track the DOTA-$Gd^{3+}$ labeled macromolecules injected in AIA rats.

It is well understood that obtaining a higher MR contrast signal intensity in the MR images represents the existence of a higher concentration of the paramagnetic contrast agents in the tissue. The analysis of the macromolecular contrast agent enhanced MR images of the rats provides important information about the pharmacokinetics profile and biodistribution of the water-soluble polymeric delivery systems described in this invention. In addition, such imaging agents will also enhance the sensitivity and anatomical resolution of the resulting images of a subject (preferably a mammal, such as a human), an animal (including, an animal model for a particular disease, dog, cat, horse or livestock), or part (e.g., a tissue or structure) of the subject or animal.

Conjugation of a low molecular weight paramagnetic contrast agent, DOTA-$Gd^{3+}$ complex to HPMA copolymer enabled the non-invasive monitoring of the fate of the injected polymer in rats with MR scanner. This approach of labeling the polymer with a MRI contrast agent is similar to labeling the polymers with fluorochromes to permit localization in organs, tissues and cells. Alternatively, this approach to imaging may also be used with other imaging agents for PET, CT and γ-scintigraphy for the purposes of non-invasive imaging, evaluation of the diseased tissues and organs and detection of molecular targets in the tissues or organs of interest, etc.

Therefore, a macromolecular magnetic resonance imaging (MRI) contrast agent based on N-(2-hydroxypropyl) methacrylamide (HPMA) copolymer has been synthesized to illustrate the invention. After systematic administration of the contrast agent in an adjuvant induced arthritis (AIA) rat model, contrast enhanced MR images were taken, which show the distribution of the polymer at different time points. Correlating the MR results with additional visual and histopathological results from the AIA rats, demonstrates the preferential deposition and retention of macromolecules in the inflamed joints. Thus, demonstrating the effectiveness of using macromolecular therapy for the treatment of rheumatoid arthritis. In addition, these results demonstrate the feasibility of using macromolecular imaging agents for imaging and evaluation of arthritic joints.

The invention includes polymeric delivery systems for the delivery of drugs, such as anti-inflammatory drugs.

The invention includes polymeric delivery systems for the delivery of imaging agents, such as chemical compounds used as enhancing agents in MRI (for example, DOTA-$Gd^{3+}$, DTPA-$Gd^{3+}$, etc.), PET (for example, compounds labeled or complexed with $^{11}C$, $^{13}N$, $^{15}O$, $^{18}F$, $^{64}Cu$, $^{68}Ga$, $^{82}Rb$, etc., such as $^{18}F$-FDG), CT (for example, iodine or barium containing compound, such as 2,3,5-triiodobenzoic acid) and γ-scintigraphy (for example, compounds complexed with $^{99}Tc$, $^{111}In$, $^{113}In$, and $^{153}Sm$, etc.) imaging.

MRI Procedure

MR images of the animals were acquired on a 1.5 T Signa LX imaging system (General Electric Medical Systems, Milwaukee, Wis.), using a phased-array coil. Images were acquired using a 3D single slab IR prepped FSPGR sequence in the coronal plane. The common imaging parameters were TR=13.4 ms, TE=2.2 ms, TI=300 ms, 25° flip angle, 512×256 in-plane acquisition matrix, 20×10 cm² field-of-view (FOV), 64 slices per slab, 1.0 mm thick slices with 2× interpolation to 0.5 mm.

Synthesis of poly(HPMA-co-APMA-co-MA-FITC).

HPMA (1 g, 7 mmol), APMA (0.14 g, 0.78 mmol), MA-FITC (0.043 g, 7.8 mmol), AIBN (0.057 g, 0.35 mmol) and MPA (0.001 mL, 1 mmol) were dissolved in methanol (10 mL), placed in an ampoule and purged with N2 for 5 minutes. The ampoule was flame-sealed and maintained at 50° C. for 24 hours. The polymer was isolated by precipitation of the resulting solution into acetone and was reprecipitated twice. After the polymer was dried in desiccator (over NaOH), the final yield was determined as 0.9 g. The content of free amino groups in the copolymer was determined as $7.7 \times 10^{-4}$ mol/g using the ninhydrin assay (18).

Synthesis of P-DOTA

Poly(HPMA-co-APMA-co-MA-FITC) (170 mg, $[NH_2]=1.33 \times 10^{-4}$ mol), DOTA-NHS ester (100 mg, $2 \times 10^{-4}$ mol) and diisopropylethyl amine (DIPEA, 160 mL, $9.33 \times 10^{-4}$ mol, distilled from ninhydrin) were mixed in DMF (1.5 mL, distilled from $P_2O_5$) and stirred overnight. The conjugate was precipitated into ether and dried in vacuum. The product was further purified on LH-20 column, dialyzed (molecular weight cutoff size is 6-8 kDa) and lyophilized to obtain 190 mg of final product. The residue free NH2 group was determined with ninhydrin assay and the content of DOTA in the product was calculated as $7.5 \times 10^{-4}$ mol/g.

Synthesis and Purification of Macromolecular MRI Contrast Agent P-DOTA-$Gd^{3+}$ P-DOTA (100 mg, $[DOTA]=6.9 \times 10^{-5}$ mol) and $GdCl_3 \cdot 6H_2O$ (38 mg, $1.04 \times 10^{-4}$ mol) were dissolved in 2 mL deionized $H_2O$. The pH of the solution was maintained at 5.0-5.5 over night by gradual addition of NaOH (1 N) solution. EDTA disodium salt (38 mg, $1.04 \times 10^{-4}$ mol) was then added into the solution to chelate the excess $Gd^{3+}$. After stirring for 30 minutes, the milky solution was purified with Sephadex G-25 column to remove the EDTA-chelated $Gd^{3+}$ and other unreacted low molecular weight compounds from the polymer conjugate. The conjugate was lyophilized to yield 115 mg P-DOTA-$Gd^{3+}$. The gadolinium content was determined by Inductively Coupled Plasma Optical Emission Spectroscopy (ICP-OES) as 0.52 mmol/g. The Mw of the polymeric MRI contrast agent is determined FPLC as 55 kDa with a polydispersity of 1.43. The $T_1$ relaxivity of the conjugate was determined as 10.4 $mM^{-1}s^{-1}$ per complexed $Gd^{3+}$ using a B1 homogeneity corrected Look-Locker technique on the 1.5 T GE NV/Cvi scanner with the LX 8.4 operating system at room temperature (19). The chemical structure of the macromolecular MRI contrast agent is shown in FIG. 1.

Synthesis of P-Dex

HPMA (1 g, 0.00698 mol), MA-GG-OH (0.156 g, 0.00078 mol), MA-FITC (0.02 g, 0.00004 mol) and AIBN (0.007 mg, 0.000043 mol) were dissolved in DMSO (1 mL) and MeOH (8 mL) mixture. The solution was transferred into an ampoule and purged with $N_2$ for 5 minutes. Then polymerized at 50° C. for 24 hours. The polymer was then reprecipitated twice to yield about 1 g of copolymer. It was further activated with a large excess of hydroxy succinimide (HOSu) and then reacted with hydrazine. After reprecipitation, dexamethasone was conjugated to the copolymer in the presence of 1 drop of acetic acid in DMF. The conjugate was purified with LH-20 column and freeze-dried to obtain the final conjugate (structure shown in FIG. 6) with dexamethasone content of 49 mg/g (of conjugate).

Adjuvant Induced Arthritis Rat Model

Male Lewis rats (175-200 g) were obtained from Charles River Laboratories (Portage, Mich.) and allowed to acclimate for at least one week. To induce arthritis, *Mycobacterium Tuberculosis* H37Ra (1 mg) and LA (5 mg) were mixed in paraffin oil (100 μL), sonicated and s.c. injected into the base of the rat's tail (20). The rats were then randomized into 3 rats/group. The progression of the joint inflammation was followed by measuring the diameter of the ankle joint with calipers. Special care was given to the rats as the inflammation developed to ensure availability and access to water and food. The MRI contrast agents used for the study were injected directly into the jugular vein while the animal was anesthetized with Ketamine and Xylazine.

Visualization of Plasma Albumin Accumulation in RA Joints

Evans blue dye (EB, 10 mg/kg in saline) was injected into healthy and AIA rats via the tail vein. The extravasation and accumulation of dye in the areas of joint inflammation could be visually observed as appearance of the blue pigment. Photographs of the ankle and paws were taken before and 8 hours after injection.

Histology

At necropsy, the major organs and limbs were removed and fixed with 10% phosphate buffered formalin for 24 hours. The organs were then dehydrated and embedded in paraffin for routine histopathological analyses. The limbs were gradually dehydrated in ascending concentrations of ethanol and embedded in poly(methyl methacrylate). Sections of the entire joint, including the undecalcified bone, were cut with a low speed saw using diamond-wafering blades. The sections were mounted on plastic slides, ground to about 50 μm in thickness and surface stained using a Giemsa stain modified for plastic sections (21). The joints (knee, ankle, tarsals and metatarsals) from the same animals that were imaged by MRI were assessed for the presence of inflammation and tissue damage using the histology sections. A Bio-quant histomorphometry system was used to measure the bone erosion surface.

Bone Mineral Density

The bone mineral density (BMD) of the bones in the arthritic joints was measured by peripheral dual x-ray absorptiometry (pDXA, Norland Medical Systems) adapted for small animals. For this the intact hind limbs were used and the scan region included the ankle and foot bones. The coefficient of variation between measurements was less than 1%.

Visual and Histological Examination of AIA Rats

The development of adjuvant-induced arthritis in the rat is well described in the literature (20), and briefly summarized here. After injection of the adjuvant, changes begin to become evident about 9 days later. This includes some inflammation around the eyes and enlarged and tender external genitalia. Inflammation and swelling of the front and hind limb ankle joints becomes evident at about 12 days after injection of the adjuvant.

At necropsy at 15 days post injection of the adjuvant, inflammation of the peritoneum (peritonitis) can be observed. Occasionally, inflammation of gastrointestinal (GI) tract and fluid retention in the peritoneal cavity are also detectable. Grossly, most of the vital organs appear to be normal except that the spleen is usually enlarged with visual evidence of inflammation.

However, under histopathological examination, all organs examined showed signs of chronic inflammation. The testicular tissue demonstrates inflammation in the membranes around the testis, with small granulomata in the epididymis being detected. The pericardial tissue demonstrates chronic inflammation, which easily could allow for build up of fluid in the pericardial tissue. The renal tissue includes multifocal areas of granulomata formation in the cortical tissue with some inflammation over the capsule, particularly along potential serosal surface changes. The splenic tissue demonstrates multifocal areas of necrosis surrounded by neutrophils and epithelioid cells. Plasma cells and lymphocytes are responding around this process, which indicate a rather severe inflammatory response throughout the splenic tissue.

Figure 2:
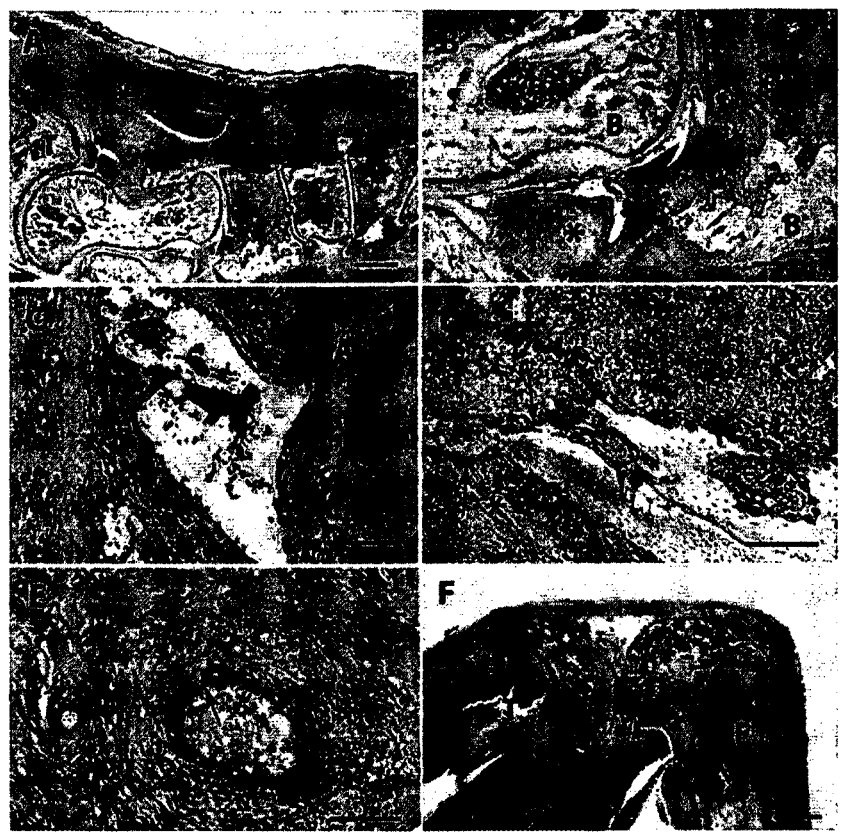
FIG. 2 shows the histology of the ankle and knee joints from the adjuvant-induced arthritis (MA) rats that were also imaged by MRI.

The histological images of the AIA rats' hind legs are presented in FIG. 2. At lower magnification, the swelling of the ankle joint region and paws of the AIA rats is evident (FIG. 2A). Extensive inflammation, synovitis, bone and cartilage destruction is evident (FIGS. 2B to 2D). Inflammatory cells are observed around the larger vessels (FIG. 2E). By contrast, the knee joints from the AIA rats are typically less affected by the inflammatory process (FIG. 2F).

Visual Examination of the AIA Rats after Evans Blue Injection

For this experiment, EB was injected into the rats 15 days after injection of the adjuvant. By this time, there is a robust inflammatory reaction evident in the ankle joints. After injection of EB, there was a gradual accumulation of blue color in the inflamed hind paw and front paws of the AIA rats with high density of the color located around the tarsus and carpus. Some deep blue spots were also observed on some digits of the paw. Photographs taken before and after injection of the EB dye confirm that the areas with dye accumulation correspond to those with marked inflammation. In the healthy control rats given EB, the dye was not localized to joint areas as observed in the AIA rats.

MR Imaging

Imaging AIA rats with P-DOTA-$Gd^{3+}$ as a contrast agent. Immediately prior to the injection of the P-DOTA-$Gd^{3+}$ contrast agent, a baseline MRI scan was done. The animals were then injected with the contrast agent and MRI scans were performed at different time intervals. The acquired images were post processed using the maximum intensity projection (MIP) algorithm. The resulting MIP images of the animals are depicted chronologically in FIG. 3.

As shown in the baseline image (FIG. 3A) before contrast injection, the intestine and stomach of the animal are clearly visible likely due to fluid retention. Several irregular spots are also observed in the lower abdomen, which can be attributed to i.p. injection site(s) of anesthetic agents. An area in the scrotum, adjacent to the testes in the anatomical region of the epididymus and associated tissue also shows a diffuse MR signal, perhaps due to its fatty content or accumulation of fluid. The bright spot at the right sciatic region may represent the fluid retention in an inconsistent lymph node called Ic. Ischiadicum, which is also evident in some of the subsequent images from this animal. No significant MR signal was observed at the hind limbs. The ankle joints were, however, clearly enlarged in the latent image when compared with similar images of the controls.

At five minutes after the injection of the macromolecular contrast agent, there was substantial MR signal in the kidneys (FIG. 3B). A detailed examination of the single-plane 2-dimensional images indicates that at this time most of the contrast agent is in the kidney cortex with little in the medulla. Because of the overall increase of the image contrast after the injection, the bladder became evident as a negative image (dark) as the oval shaped structure at lower left abdominal area. Increased contrast is also observed in the liver, spleen and bone marrow. The major blood vessels are clearly defined while the lesser vessels are not as apparent, probably due to the limited imaging resolution (about 0.5 mm) with the 1.5 T MRI scanner. However, the vessels appear larger, perhaps dilated, than those observed in the healthy controls. Except for some uptake in the bone marrow, little significant contrast signal was evident at this time in the inflamed ankle region.

In the MR images (FIG. 3C) of the AIA rats acquired 1 hour post injection, the signal in the cortex of kidneys was greatly reduced compared with the earlier (5 minute) time. However, now most of the contrast appears to be concentrated in the kidney medulla and pelvis. Both ureters contain contrast material and a substantial signal is now evident in the urinary bladder. There appeared to be slight decrease in the MR contrast signal in the liver, spleen and blood vasculature. Interestingly, several "hot spots" start to appear around the tarsus, where the most severe inflammation occurs in this animal model.

From the MR images acquired 2 hours (FIG. 3D) and 3 hours (FIG. 3E) post injection of the macromolecular contrast agent, a gradual reduction of MR contrast signal was evident in the kidney (cortex and medulla), liver, spleen and vasculature. There was, however, an accumulation of the contrast material in the urinary bladder. The "hot spots" detected around the tarsus at the 1 hour scan continue to expand and increase in contrast in the 2 hours (FIG. 4-B) and 3 hours images.

When the rats were scanned again at 8 hours post injection, the MR images (FIG. 3F) acquired show greatly reduced MR signal in all the vital organs and blood vessels with essentially an undetectable bladder, even though the overall body signal remains slightly greater than that of the baseline images. Surprisingly, however, the MR contrast signal is substantially increased in the ankle joint and metatarsal region (FIG. 4C). The initial "hot spots" disappear and the MR contrast signal is more evenly distributed around the joint tissue. Also observed is some contrast signal in the posterior knee joints, but with a much less intensity and size (FIG. 4 D).

Subsequently, the animals were again scanned at 32 hours and 48 hours post injection, respectively (FIGS. 3G and 3H). The overall contrast enhancement of MR signal continued to decline from that observed in the 8 hr images. However, the decrease in image contrast in the ankle joint tissue appeared to be much slower than observed in other tissues and organs. Even after 48 h, the enhancing effect of the injected macromolecular contrast agents is still visible in the hind ankle and paw tissue.

Imaging healthy rats with P-DOTA-$Gd^{3+}$ as a contrast agent. In the MR images (FIG. 3J) taken 5 minutes after the injection of macromolecular contrast agent, the kidneys of the healthy animals showed extremely strong contrast signal. The single-plane 2-D images indicate that the MR contrast resides in both the cortex and medulla. Both side ureters are partially visible. The urinary bladder is filled with a significant amount of contrast medium. Liver, spleen and bone marrow were visible in the image when compared with the baseline image. The major blood vessels, including the abdominal aorta and inferior vena cava were also highlighted. The arrangement and appearance of these vessels appears to be normal. No contrast signal was detected outside of the large vessels in the hind paws.

In the MR images taken at 1 hour (FIG. 3K) and 2 hours (FIG. 3L) post injection, little contrast media remains in the kidney cortex and medulla, but some contrast signal remained in the kidney pelvis and bladder. The contrast enhancement of the vasculature was slightly reduced compared with that observed at 5 minutes after injection. At 8 hours (FIG. 3M) after injection, the contrast media was completely cleared from the urinary tract. At this time, some of the large vessels were still evident, though less so than at earlier times. The images taken at 48 hours (FIG. 3N) after injection replicate the baseline images with no detectable contrast enhancement. As expected, all MR images taken at different times post injection did not show contrast enhancement in the hind-limb joints of the animal.

Imaging AIA and Healthy Rats with OMNISCAN as Contrast Agent.

The images acquired with the MR enhancement of a low molecular weight paramagnetic contrast agent OMNISCAN (gadolinium complex of diethylenetriamine pentaacetic acid bismethylamide) were obtained similarly as those injected with P-DOTA-$Gd^{3+}$.

Figure 3:
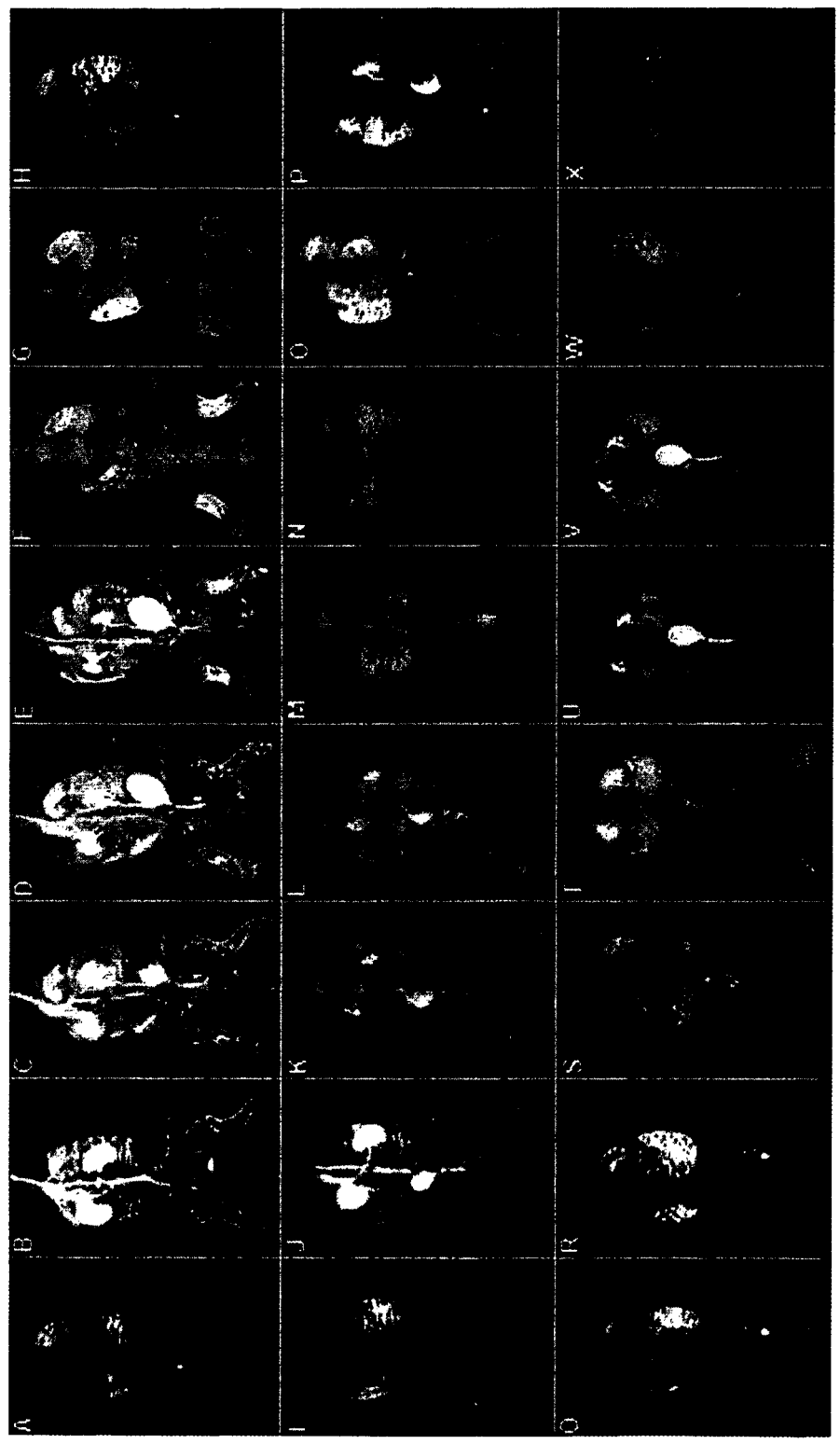
FIG. 3 shows the MR images of the animals taken at different time points. The acquired images were post processed using the maximum intensity projection (MIP) algorithm.
Figure 4:
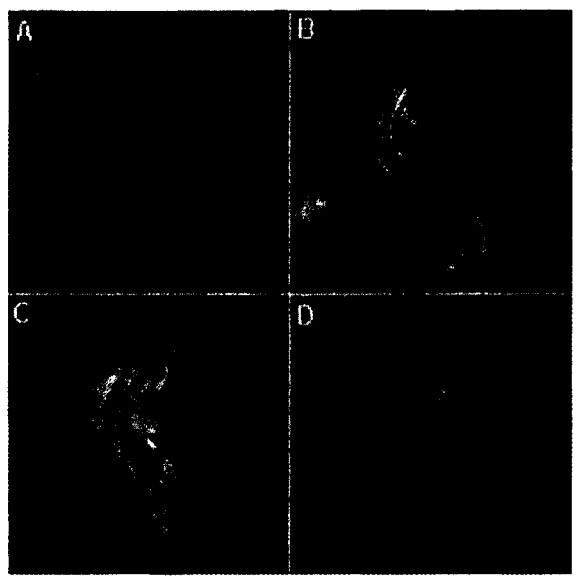
FIG. 4 illustrates single-plane MR imaging of AIA rats injected with P-DOTA-$Gd^{3+}$.

From the image sequence presented in FIGS. 3 (3O to 3X), a very fast overall tissue contrast enhancement at 5 minutes post injection was observed in both healthy and AIA rats (FIGS. 3O & 3T). However, the contrast enhancement quickly declined, accompanied by a rapid renal clearance of the contrast medium. At 8 hours (FIGS. 3Q & 3W), the enhancement was basically gone. Interestingly, the 5-minute images (FIG. 3O) of the AIA rats reveal significant contrast enhancement at the inflamed ankle joints, which had cleared at the 2 hours scan (FIG. 3P). However, no such observation was found in the healthy rats. Basically, no blood vasculature contrast enhancement could be observed in all OMNISCAN enhanced MR images.

As shown in FIG. 3, all vital organs in AIA rats showed greater uptake of P-DOTA-$Gd^{3+}$ than the healthy rats. In addition, the clearance of the contrast agent in these organs was slower than those in healthy rats, especially in the kidneys. These observations are consistent with the histological findings that all organs in AIA rats, including heart, liver, lung, kidney and spleen had some granulomatous chronic inflammation. The vasculature in such inflamed tissues is often more porous, permitting a greater extravasation of macromolecules to the interstitial tissue. These may lead to organ dysfunction, such as the delayed renal clearance of the polymer contrast agent compared to healthy rats. However, the major clearance of P-DOTA-$Gd^{3+}$ from these organs was completed within a few hours (<8 h) in the AIA rats. When compared with normal rats, the major blood vessels appear to be dilated in the AIA rats. This observation may be due to the up-regulated prostaglandins level in this systematic inflammation model (26). It may also help to explain the observed faster polymer extravasation.

Interestingly however, extravasation in the inflamed ankle joints was delayed for a short time (1~2 h) in the AIA model (FIGS. 3A-3H). The "hot spots" of high MR contrast signal appeared later around the tarsus indicating high local concentrations of P-DOTA-$Gd^{3+}$. These "hot spots" also reveal the locations of possible local damage in and around the joint. The polymer continues to extravasate, diffuse, accumulate in the ankle joints and the greatest concentrations were observed in the 8 hours post injection images (single plane, enlarged MR images, FIG. 4). Because some increased concentrations of polymer were still observed in the joint at 32 hours after injection, it appears that the clearance of the polymer from the joint is relatively slow. By correlating the polymer accumulation, as detected by MRI, with the histology of the same tissues (FIGS. 2A, 2B and 2D), it is evident that the accumulation of the polymer correlates with the degree of inflammation. As observed in the 8 hours MR images, the accumulation of P-DOAT-$Gd^{3+}$ to the knee joints was much less than that observed to the ankle joints (FIG. 4D). This finding agrees very well with the amounts and degree of severity of inflammation observed histologically in the joints (FIG. 2F). In contrast to the observation with AIA rats, no extravasation of P-DOTA-$Gd^{3+}$ to the ankle or knee joints was observed in the healthy control rats.

The data suggests a pharmacokinetic profile with a renal clearance mechanism and a redistribution of the HPMA copolymer (labeled with DOTA-$Gd^{3+}$) from major organs and the blood circulation compartment into the inflammatory arthritic joints. Compared to the normal animal, the result from the MR images of the AIA model clearly demonstrate a very selective polymer targeting and accumulation effect to the arthritic joints with a time frame of about 1 to 2 days after a single bolus injection. Given that most current anti-arthritic drugs do not specifically target the arthritic joints and the damaged tissues, coupled with a low efficacy, the observed targeting and accumulation of the polymeric delivery systems to arthritic joints demonstrate the great effectiveness and numerous potential applications of this invention for the drug delivery and treatment, for example, of rheumatoid arthritis.

Likewise, imaging and evaluation of the inflammatory tissues or organs, such as arthritic joints, with an MRI macromolecular contrast agent, also provides much improved imaging results, as shown in FIGS. 3F & 4C, when compared to the low molecular weight MRI contrast agent, such as OMNISCAN (FIG. 3O). The invention permits a greater time frame for longer and/or more detailed and/or sophisticated imaging process, which can't be, or are not optimally, performed with the current low molecular weight imaging agents, such as OMNISCAN. More anatomical detail can be revealed with these imaging agents, which may have many applications, such as preclinical evaluation of therapeutic effects of experimental anti-arthritic drugs on an animal model and clinical evaluation of patient response to treatment. Similar benefits may be realized when using the invention with PET, CT or γ-scintigraphy imaging agents. When MRI, PET, CT or γ-scintigraphy imaging agents are conjugated to the polymeric delivery systems described in this invention, they will be able to provide powerful molecular imaging tools for the understanding of inflammatory diseases, such as rheumatoid arthritis.

While the enhanced permeability of the vasculature in the arthritic joints may be comparable to those found in solid tumor, the retention of the polymer in the joint tissue may vary according to the stage of the disease. A swift drug-cleavage mechanism may be applied to ensure effective release of the drug from the macromolecular carrier. A person of ordinary skill in the art will recognize that some pathological features of the arthritic joints may be exploited for this. For example, the release of the drug from the polymer may be facilitated by things such as the very high extracellular enzyme activities (e.g., cathepsin K, MMPs, etc.) (28), low pH, hypoxia or elevated temperature (29). Likewise, measures that would enhance the retention of the extravasated polymers in the joints may also be used according to the invention (e.g., the polymer drug conjugates). Incorporation of targeting moieties, which would bind to the negatively charged cartilage (30), the freshly eroded bone surface (21) or the enriched rheumatic factors in the RA joints may also be used to increase the uptake and retention of the polymer in joint tissue. It is also believed that by increasing the molecular weight of the polymeric carrier, a greater retention of the polymer in the RA joint may be accomplished. Anti-arthritic drugs, such as glucocorticoids, can be used in the drug delivery system of the invention.

As will be recognized by a person of ordinary skill in the art, anti-inflammatory drugs, anti-arthritic drugs, targeting moieties, and imaging agents, as used herein, include acceptable salts, esters, or salts of such esters. For example, glucocorticoids include pharmaceutically acceptable salts and esters thereof, therefore, when a drug is described, e.g., dexamethasone, pharmaceutically acceptable salts thereof are also described, such as dexamethasone palmitate.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts and acid addition salts are known in the art (see, for example, Berge et al., "Pharmaceutical Salts," *J. of Pharma Sci.*, 1977, 66, 1-19; REMINGTON'S PHARMACEUTICAL SCIENCES, 18th Ed. (1990, Mack Publishing Co., Easton, Pa.); and GOODMAN AND GILMAN'S, THE PHARMACOLOGICAL BASIS OF THERAPEUTICS (10th ed. 2001)).

The term "prodrug" indicates a therapeutic agent that is prepared in an inactive form that is converted to an active form (i.e., drug) within the body or cells thereof by the action of endogenous enzymes or other chemicals and/or conditions.

In addition, currently available protein drugs and orally available low molecular weight drug may also benefit from the principles illustrated in the invention. For example, the extravasation of the injected polymer into the RA joints was delayed for 1 to 2 hours. Thus, for the protein or peptide drugs, they must survive this period of time against hepatic and renal clearance. Protein or peptide drugs may be stabilized by methods known in the art, for example, PEGylation of the protein and/or modification of the polymer backbone may provide a beneficial means in solving this problem (3).

Using modern MR imaging techniques, the specific accumulation of macromolecules was observed in arthritic joints in the rat model of adjuvant-induced arthritis. There was an excellent correlation between the uptake and retention of the MR contrast agent labeled polymer with histopathological features of inflammation and local tissue damage. The methodology used in this study proved that macromolecular imaging agents (polymeric delivery systems conjugated with MRI, CT PET, γ-scintigraphy imaging agents) are powerful imaging and evaluation tools for inflammatory diseases, such as rheumatoid arthritis. The use of the macromolecular imaging agents also demonstrates the utility of the delivery system for the purpose of targeting a drug, which is a beneficial improvement over current treatments, for example, for treating rheumatoid arthritis. The invention provides the ability to increase the therapeutic potential and dosing window of the drugs by reducing their side effects. Furthermore, the invention may have a longer half-life in blood circulation when compared to low molecular weight drugs, which may increase the bioavailability of the drug. In addition, the invention may be used to render a hydrophobic drug hydrophilic and, particularly for peptide-based drugs, reduce immunogenecity.

Figure 6:
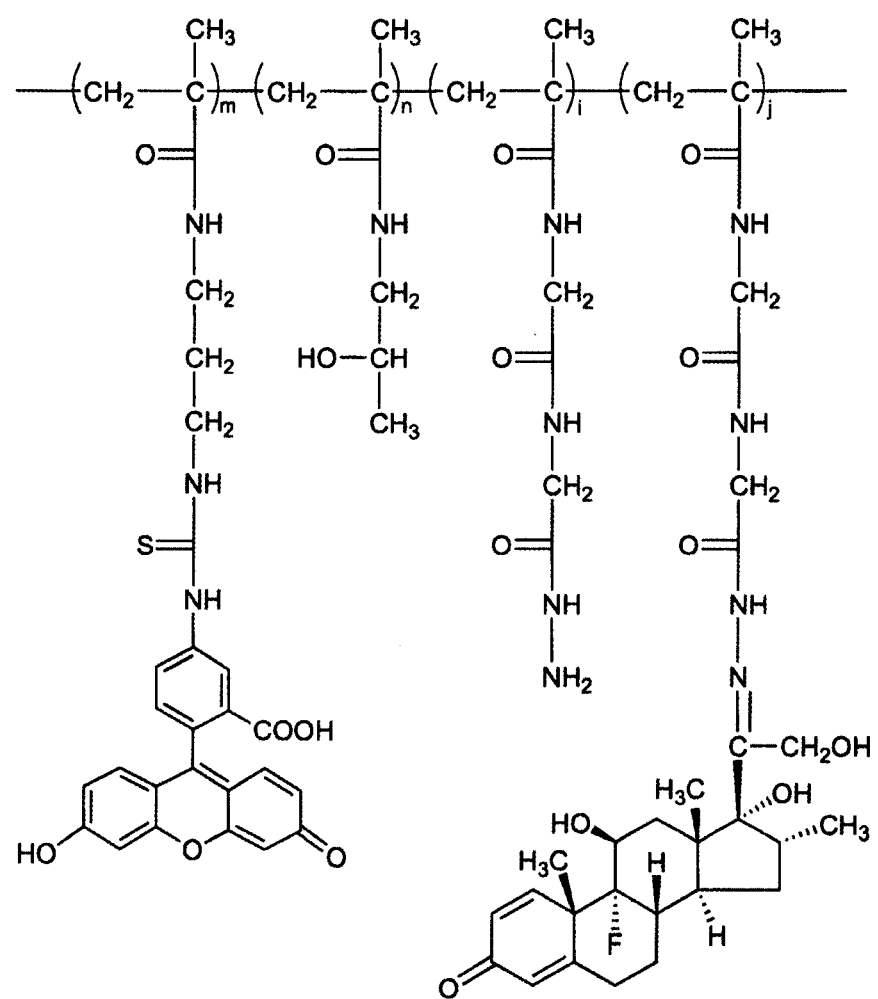
FIG. 6 illustrates the chemical structure of a exemplary polymeric drug delivery system, with dexmethasone as an example of a therapeutic agent, for the treatment of arthritis. The polymeric prodrug is abbreviated as P-Dex.
Figure 7:
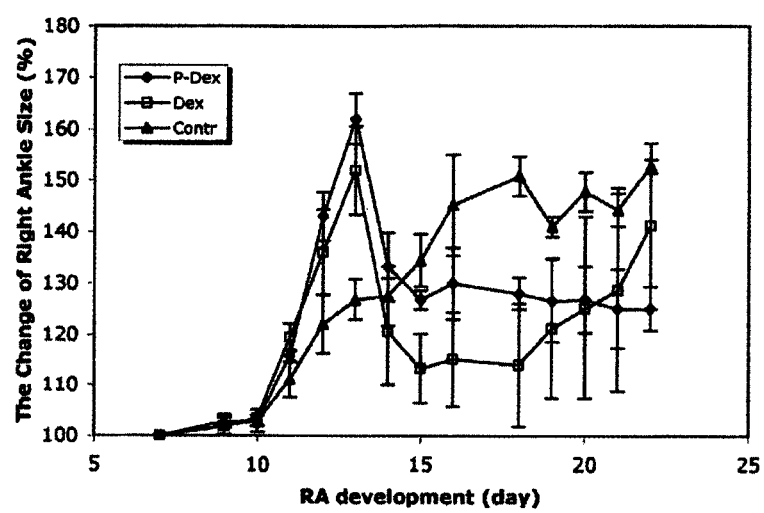
FIG. 7 shows the superior therapeutic effect of P-Dex over dexamethasone sodium phosphate (Dex) in reducing the size of the inflamed arthritic joints during treatment.

To demonstrate the superior therapeutic effects of the invention, a HPMA copolymer containing targeting moiety with an anti-arthritic drug was synthesized. Hydrazine was used as the targeting moiety, as it may bind to negative charged moieties on cartilage. The anti-arthritic drug, dexamethasone, was linked to the polymer backbone (P-Dex) via a pH sensitive hydrozone bond as illustrated in FIG. 6. The polymer with the hydrazine and dexamethasone attached was then injected into AIA rats (4/group) on day 13 after the induction of arthritis. A single dose of 10 mg (P-Dex)/kg was given. As a control, the same dose of low molecular weight Dexamethasone sodium phosphate (Dex) was divided into 4 equal doses and one dose was given each day to another group of AIA rats (4/group) from day 13-16 after the induction of arthritis. As shown in FIG. 7, both groups of animals showed a dramatic decrease of ankle joint swelling after the injections on day 13. However, with the cessation of the daily injections of the control Dex, the inflammation rapidly got worse while the inflammation in the P-Dex group had a prolonged suppression. These significant advantages of the P-Dex treatment may be attributed to the specific targeting and enhanced retention (because of the cartilage targeting moiety) of the polymeric delivery system to the arthritic joints of the animals.

Figure 8:
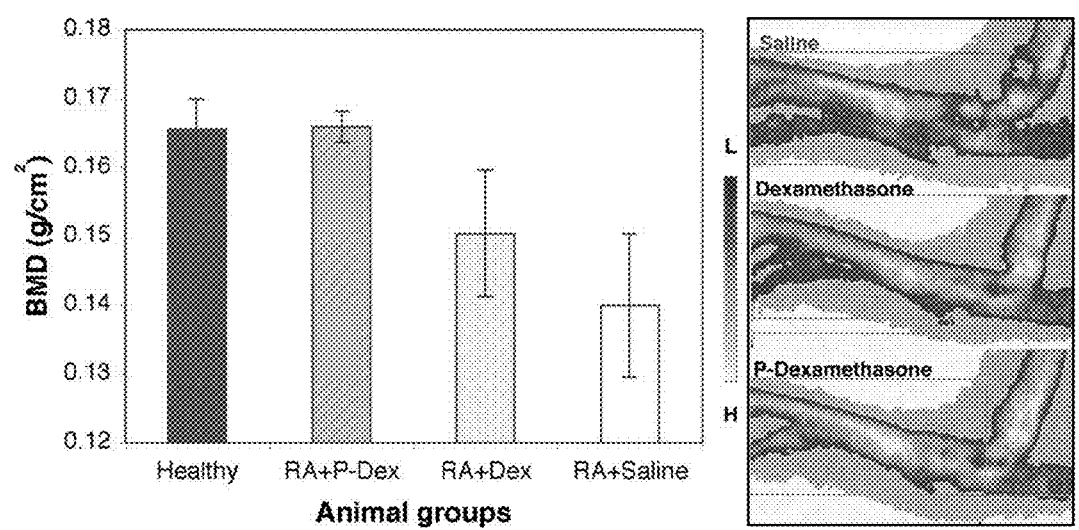
FIG. 8 shows the superior therapeutic effect of P-Dex over dexamethasone sodium phosphate (Dex) in the bone mineral density (BMD) of the inflamed arthritic joints during treatment. The results were obtained by dual x-ray absorptiometry (DEXA).
Figure 9:
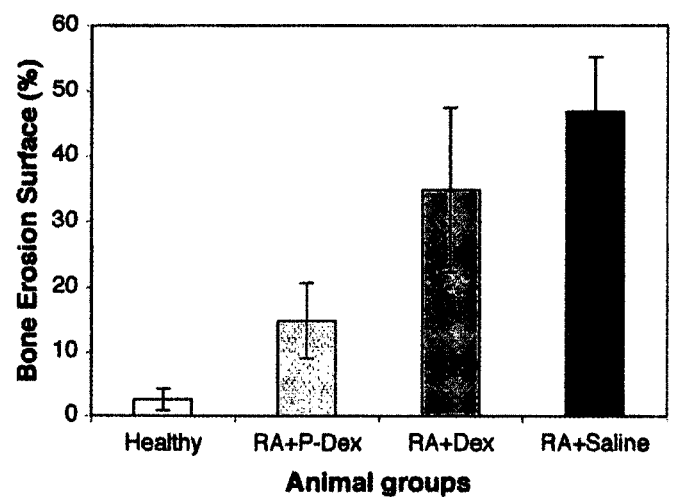
FIG. 9 shows the superior therapeutic effect of P-Dex over dexamethasone sodium phosphate (Dex) in reducing erosion of the bone surface of inflamed arthritic joints during treatment. The results were obtained by histomorphometry using a Bioquant image analysis system.
Figure 10:
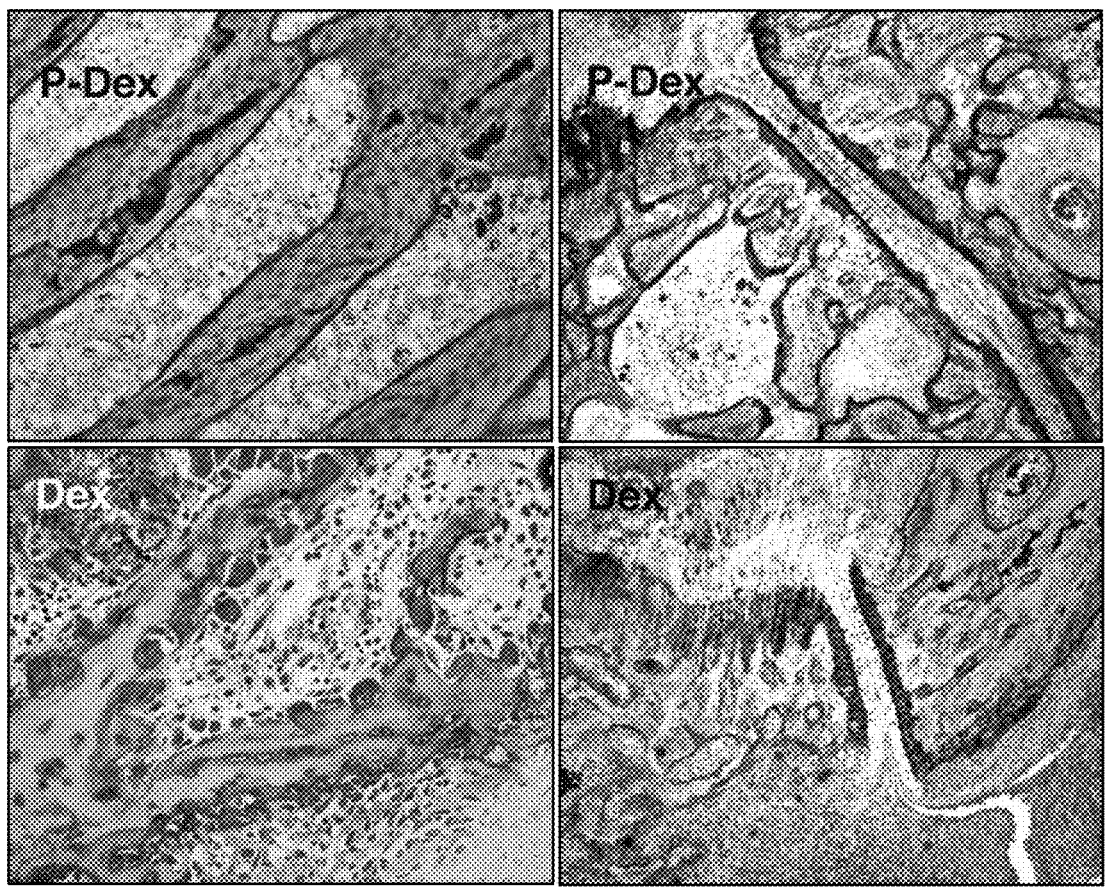
FIG. 10 shows the superior therapeutic effect of P-Dex over dexamethasone sodium phosphate (Dex) by histological observation of the inflamed arthritic joints during treatment.

To strengthen the statistics of the observed superior therapeutic effects of the delivery system, a study with larger animal groups (7/group) was performed. One of the significant impacts of rheumatoid arthritis inflammation is the damage to the bone in the joints, which is evident in FIG. 8 of the animals with no treatment (saline). Glucocoticoids, such as dexamethasone (Dex), can slow bone erosion by reducing the inflammation of the joints, as evident in FIG. 8 of animals with Dex treatment. However, such improvement can be greatly strengthened if Dex is conjugated to HPMA copolymer. The inhibition of inflammation is prolonged (FIG. 7.) and the bone is well preserved in the P-Dex treated animal group with a BMD similar to the healthy group. A more dynamic factor to consider in the bone metabolism is the extent of bone erosion. The bone eroded surface directly correlates with the recruitment and activity of osteoclasts, which are the cells responsible for bone resorption and the development of bone damage. In FIG. 9, the bone erosion surface data for all the treatment groups is summarized. Again, the P-Dex group showed a lower percentage of erosion surface compare to the Dex group. The histology analysis of the arthritic joints with different treatments also confirmed the superiority of the P-Dex treatment (FIG. 10).

A water-soluble polymer backbone of the invention includes, but is not limited to, a HPMA copolymer and its derivatives, polyethylene glycol (including branched or block copolymers, which may be degradable via peptide sequences, ester or disulfide bonds, etc.), polyglutamic acid, polyaspartic acid, dextran, chitosan, cellulose and its derivatives, starch, gelatin, hyaluronic acid and its derivatives, polymer or copolymers of the following monomers: N-isopropylacrylamide, acrylamide, N,N-dimethylacrylamide, N-vinylpyrrolidone, vinyl acetate (resulting polymer hydrolyzed into polyvinyl alcohol or PVA), 2-methacryloxyethyl glucoside, acrylic acid, methacrylic, vinyl phosphonic acid, styrene sulfonic acid, maleic acid, 2-methacrylloxyethyltrimethylammonium chloride, methacrylamidopropyltrimethyl-ammonium chloride, methacryloylcholine methyl sulfate, N-methylolacrylamide, 2-hydroxy-3-methacryloxypropyltrimethyl ammonium chloride, 2-methacryloxyethyl-trimethylammonium bromide, 2-vinyl-1-methylpyridinium bromide, 4-vinyl-1-methylpyridinium bromide, ethyleneimine, (N-acetyl)ethyleneimine, (N-hydroxyethyl) ethyleneimine and/or allylamine. Preferably, the water-soluble polymer is biologically inert, however, optionally the polymer may have therapeutic activity (31).

The invention may, optionally, include one or more targeting moieties, which may be used to direct the delivery system to a specific tissue, such as bone, cartilage, etc. Illustrative examples of targeting moieties include, but are not limited to, bisphosphonates, quaternary ammonium groups, peptides (e.g., oligo-Asp or oligo-Glu), aminosalicylic acid, and/or antibodies or fragments or derivatives thereof (e.g., Fab, humanized antibodies, and/or scFv). A targeting moiety may be linked to the polymer backbone via covalent or physical bonds (linkages). Optionally, the spacers between a targeting moiety and the polymer backbone may be cleaved upon a stimulus including, but not limited to, changes in pH, presence of a specific enzyme activity (for example, cathepsin K, MMPs, etc.), changes in oxygen levels, etc.

Optionally, the spacers between the therapeutic agent and the polymer backbone may be cleaved upon a stimulus including, but not limited to, changes in pH, presence of a specific enzyme activity (for example, cathepsin K, MMPs, etc.), changes in oxygen levels, etc.

Optionally, a bio-assay label (or labels) may be attached to the polymer backbone. It may be any label known in the art, including, but not limited to, a radioisotope, biotin, gold, etc. Their average mol percentage per polymer chain may range from 0% to about 50%.

The bio-assay label, therapeutic agent, and/or targeting moiety may be linked to the water-soluble polymer backbone by way of a spacer. Spacers are known in the art and the person of ordinary skill in the art may select a spacer based on length, reactivity, flexibility and the like. For example, a spacer may be an alkyl or alkyne having from one to 50, preferably one to 15 carbons.

A spacer of the invention may be a peptide sequence (for example, selected from all nature amino acids) having from one to 20, preferably one to 10 residues. In yet another example, a spacer may contain a hydrozone bond which is cleavable under acidic pH. These spacers may be cleaved upon a stimulus including, but not limited to, changes in pH, presence of a specific enzyme activity (for example, cathepsin K, MMPs, etc.), changes in oxygen levels, etc.

Optionally, the biodegradable cross-linkage shown in FIG. 5 may cross-link, to a certain degree, the linear polymer backbone. The resulting delivery system still retains its water-solubility. The linkage itself is preferably cleavable under physiological conditions.

As will be appreciated by a person of ordinary skill in the art, each class (e.g., therapeutic agent, targeting moiety, bio-assays label, spacer and/or imaging agent) may comprise any number of different compounds or compositions. For example, the therapeutic agent may consist of a mixture of one or more NSAIDs and one or more glucocorticoid, such as a combination of dexamethasone and hydrocortisone. Therefore, the invention provides the advantage that any combination of different therapeutic agents, targeting moieties, bio-assays labels, spacers and/or imaging agents may be incorporated onto the water-soluble polymer backbone. As a result, a drug delivery or imaging system can be created with two or more different therapeutic agents and/or two or more different targeting moieties and/or two or more different bio-assays labels, and/or two or more different spacers (one or more of which may be cleavable, wherein the cleavage stimulus may be different for different spacers) and/or two or more imaging agents. For example, one or more imaging agents may be combined with one or more therapeutic agents, to produce a drug/imaging agent combination, which, for example, may be used to treat and/or monitor the subject. One exemplary embodiment of such an drug/imaging agent is a method of determining the effects of a particular drug or drug combination. For example, the drug/imaging agent may contain a candidate drug wherein the imaging agent allows for enhanced monitoring of the candidate drugs effects. In another exemplary embodiment, the drug/imaging agent may also be used to treat a subject and to monitor the subjects response to the treatment.

An effective amount of a drug is well known in the art and changes due to the age, weight, severity of a subject's condition, the particular compound in use, the strength of the preparation, and the mode of administration. The determination of an effective amount is preferably left to the prudence of a treating physician, but may be determined using methods well known in the art (37, 38). The compositions of the invention may be prepared using methods known in the art, for example, the preparation of a pharmaceutical composition is known in the art (37, 38).

The compositions may be administered by any desirable and appropriate means. For in vivo delivery (i.e., to a subject having arthritis or other inflammatory diseases), it is preferred that the delivery system be biocompatible and preferably biodegradable and non-immunogenic. In addition, it is desirable to deliver a therapeutically effective amount of a compound in a physiologically acceptable carrier. Injection into an individual may occur subcutaneous, intravenously, intramuscularly, intraperitoneal, intraarticular or, for example, directly into a localized area. Alternatively, in vivo delivery may be accomplished by use of a syrup, an elixir, a liquid, a tablet, a pill, a time-release capsule, an aerosol, a transdermal patch, an injection, a drip, an ointment, etc.

ABBREVIATIONS

AIA, adjuvant induced arthritis; AIBN, 2,2'-azobisisobutyronitrile; APMA, N-(3-Aminopropyl)methacrylamide hydrochloride; BMD, bone mineral density; COX-2, cycloxygenase-2; CT, computerized tomography; Dex, Dexamethasone sodium phosphate; DMARDs, disease-modifying antirheumatic drugs; DIPEA, diisopropyl ethyl amine; DOTA, 1,4,7,10-tetraazacyclododecane-1,4,7,10-tetra (acetic acid); DOTA-NHS ester, 1,4,7,10-tetraazacyclododecane-1,4,7-tris(acetic acid)-10-acetic acid mono (N-hydroxysuccinimidyl ester); DTPA-$Gd^{3+}$, gadolinium complex with diethylenetriamine pentaacetic acid; DXA, dual x-ray absorptiometry; EB, Evans blue; EPR, enhanced permeability and retention; $^{18}$F-FDG, fluorodeoxyglucose; FITC, fluorescein isothiocyanate; FPLC, fast protein liquid chromatography; HPMA, N-(2-hydroxypropyl)methacrylamide; ICP-OES, inductively coupled plasma optical emission spectroscopy; IL-1Ra, interleukin-1 receptor antagonist; LA, N,N-dioctadecyl-N',N'-bis(2-hydroxyethyl) propanediamine; MA-FITC, N-methacryloylaminopropyl fluorescein thiourea; MA-GG-$NHNH_2$, N-methacryloyl glycylglycyl hydrazine; Mn, number average molecular weight; MPA, mercaptopropionic acid; MRI, magnetic resonance imaging; Mw, weight average molecular weight; NSAIDs, symptomatic treatment with non-steroidal anti-inflammatory drugs; OA, osteoarthritis; OMNISCAN, or gadodiamide is the injectable formulation of the gadolinium complex of diethylenetriamine pentaacetic acid bismethylamide; P-Dex, conjugate of dexamethasone to copolymer of HPMA, MA-GG-$NHNH_2$ and MA-FITC via hydrozone bond (FIG. 6.); PET, positron emission tomography; PHPMA, poly[N-(2-hydroxypropyl)methacrylamide]; Poly(HPMA-co-APMA-co-MA-FITC), copolymer of HPMA, APMA and MA-FITC; P-DOTA, conjugation product of poly(HPMA-co-APMA-co-MA-FITC) and DOTA-NHS ester; P-DOTA-$Gd^{3+}$, purified complex of P-DOTA and $Gd^{3+}$; RA, rheumatoid arthritis; R.T., room temperature; SEC, size exclusion chromatography; scFv, single chain variable fragment; TMJ, temporomandibular joint syndrome; TNF, tumor necrosis factor.

All references, including publications, patents, and patent applications, cited herein are hereby incorporated by reference to the same extent as if each reference were individually and specifically indicated to be incorporated by reference and were set forth in its entirety herein. The following list of references are hereby incorporated by reference:

REFERENCES

1. G. S. Firestein. Etiology and Pathogenesis of Rheumatoid Arthritis. In S. Ruddy, E. D. Harris Jr. and C. B. Sledge (ed.) *Kelley's Textbook of Rheumatology*, 6$^{th}$ Ed. W.B. Saunders Company, St. Louis, 1997, pp 921.

2. F. C. McDuffie. Morbidity impact of rheumatoid arthritis in society. *Am. J. Med.* 78:1-5 (1985).

3. J. S. Smolen and G. Steiner. Therapeutic strategies for rheumatoid arthritis. *Nature Review Drug Discovery* 2:473-488 (2003).

4. W. J. Wallis, P. A. Simkin and W. B. Nelp. Protein traffic in human synovial effusion. *Arthritis and Rheumatism* 30:57-63 (1987).

5. J. R. Levick. Permeability of rheumatoid and normal human synovium to specific plasma proteins. *Arthritis and Rheumatism* 24:1550-1560 (1981).

6. M. Albuquerque and J. P. de Lima. Articular lymphoscintigraphy in human knees using radiolabeled dextran. *Lymphology* 23:215-218 (1990).

7. L. S. Wilkinson and J. C. W. Edwards. Demonstration of lymphatics in human synovial tissue. *Rheumatol. Int.* 11:151-155 (1991).

8. E. L. Matteson. Current treatment strategies for rheumatoid arthritis. *Mayo Clin. Proc.* 75:69-74 (2000).

9. E. Santana-Sahagun and M. H. Weisman. Nonsteroidal Anti-inflammatory Drugs. In S. Ruddy, E. D. Harris Jr. and C. B. Sledge (ed.) *Kelley's Textbook of Rheumatology*, 6$^{th}$ Ed. W.B. Saunders Company, St. Louis, 1997, pp 799-822.

10. C. M. Stein and T. Pincus. Glucocorticoids. In S. Ruddy, E. D. Harris Jr. and C. B. Sledge (ed.) *Kelley's Textbook of Rheumatology*, 6$^{th}$ Ed. W.B. Saunders Company, St. Louis, 1997, pp 823-840.

11. J. Kopeček, P. Kopečková, T. Minko and Z. R. Lu. HPMA copolymer-anticancer drug conjugates: design, activity, and mechanism of action. *Eur. J. Pharm. Biopharm.* 50:61-81 (2000).

12. L. W. Seymour. Passive tumor targeting of soluble macromoleculaes and drug conjugates. *Critical Reviews In Therapeutic Drug Carrier Systems* 9:135-187 (1992).

13. J. M. Metselaar, M. H. Wauben, J. P. Wagenaar-Hilbers, O. C. Boerman and G. Storm. Complete remission of experimental arthritis by joint targeting of glucocorticoids with long-circulating liposomes. *Arthritis Rheum.* 48:2059-2066 (2003).

14. M. N. J. Paley, I. D. Wilkinson, E. van Beek and P. D. Griffiths. Magnetic resonance imaging: basic principles. In R. G. Grainger, D. Allison, A. Adam and A. K. Dixon (ed.) *Grainger & Allison's Diagnostic Radiology: A Textbook of Medical Imaging*, 4$^{th}$ Ed. Churchill Livingstone, Inc. London, 2001, pp 101-136.

15. J. Kopeček and H. Bazilová. Poly[N-(2-hydroxypropyl) methacrylamide]. I. Radical polymerization and copolymerization. *Eur. Polym. J.* 9:7-14 (1973).

16. V. Omelyanenko, P. Kopečková, C. Gentry and J. Kopeček. Targetable HPMA copolymer-adriamycin conjugates. Recognition, internalization, and subcellular fate. *J. Controlled Release* 53:25-37 (1998).

17. T. H. Cronin, H. Faubl, W. W. Hoffman and J. J. Korst. Xylene-diamines as antiviral agents. U.S. Pat. No. 4,034,040, 1977.

18. S. Moore and W. H. Stein. A modified ninhydrin reagent for the photometric determination of amino acids and related compounds. *J. Biol. Chem.* 211:907-913 (1954).

19. Z. R. Lu, X. Wang, D. L. Parker, K. C. Goodrich, H. R. Buswell. Poly(l-glutamic acid) Gd(III)-DOTA conjugate with a degradable spacer for magnetic resonance imaging. *Bioconjug Chem.* 14:715-719 (2003).

20. A. M. Bendele. Animal models of rheumatoid arthritis. *J. Musculoskel. Neuron. Interact.* 1:377-385 (2001).

21. D. Wang, S. C. Miller, M. Sima, P. Kopečková, and J. Kopeček. Synthesis and evaluation of water-soluble polymeric bone-targeted drug delivery systems. *Bioconjug. Chem.* 14:853-859 (2003).

22. I. Kushner and J. A. Somerville. Permeability of human synovial membrane to plasma proteins. Relationship to molecular size and inflammation. *Arthritis and Rheumatism* 14:560-570 (1971).

23. T. P. Jacobs, O. Kempski, D. McKinley, A. J. Dutka, J. M. Hallenbeck, G. Feuerstein. Blood flow and vascular permeability during motor dysfunction in a rabbit model of spinal cord ischemia. *Stroke* 23:367-373 (1992).

24. Y. Matsumura, H. Maeda. A new concept for macromolecular therapeutics in cancer chemotherapy: mechanism of tumoritropic accumulation of proteins and the antitumor agent smancs. *Cancer Res.* 46:6387-6392 (1986).

25. M. A. Brown and R. C. Semelka. Principles of Magnetic Resonance Imaging. In M. A. Brown and R. C. Semelka (ed.) *MRI: Basic Principles and Applications*, 3$^{rd}$ Ed. Wiley-Liss, New York, 2003, pp 27-42.

26. D. Claveau, M. Sirinyan, J. Guay, R. Gordon, C. C. Chan, Y. Bureau, D. Riendeau and J. A. Mancini. Microsomal prostaglandin E synthase-1 is a major terminal synthase that is selectively up-regulated during cyclooxygenase-2-dependent prostaglandin E2 production in the rat adjuvant-induced arthritis model. *J. Immunol.* 170:4738-4744 (2003).

27. M. I. V. Jayson and A. St. J. Dixon. Intra-articular pressure in the rheumatoid arthritis of knee. I. Pressure changes during passive joint distension. *Ann. Rheum. Dis.* 29:261-265 (1970).

28. Y. Okada. Proteinases and Matrix Degradation. In S. Ruddy, E. D. Harris Jr. and C. B. Sledge (ed.) *Kelley's Textbook of Rheumatology*, 6$^{th}$ Ed. W.B. Saunders Company, St. Louis, 1997, pp 55-72.

29. P. S. Treuhaft and D. J. McCarty. Synovial fluid pH, lactate, oxygen and carbon dioxide partial pressure in various joint diseases. *Arthritis and Rheumatism* 14:475-484 (1971).

30. I. Giraud, M. Rapp, J. C. Maurizis and J. C. Madelmont. Application to a cartilage targeting strategy: synthesis and in vivo biodistribution of 14 C-labeled quaternary ammonium-glucosamine conjugates. *Bioconjug. Chem.* 11:212-218 (2000).

31. M. Rapp, Giraud I., Maurizis J. C., Galmier M. J., Madelmont J. C. Synthesis and in vivo biodisposition of [14C]-quaternary ammonium-melphalan conjugate, a potential cartilage-targeted alkylating drug. *Bioconjug Chem.* 14(2):500-6 (2003).

32. A. Wunder, Muller-Ladner U., Stelzer E. H., Funk J., Neumann E., Stehle G., Pap T., Sinn H., Gay S., Fiehn C. Albumin-based drug delivery as novel therapeutic approach for rheumatoid arthritis. *J. Immunol.* 170(9):4793-801 (2003).

33. S. L. Timofeevski, Panarin E. F., Vinogradov O. L., Nezhentsev M. V. Anti-inflammatory and antishock water-soluble polyesters of glucocorticoids with low level systemic toxicity. *Pharm Res.* 13(3):476-80 (1996).

34. H. Kitamura, Kato A., Esaki T. AG-041R, a novel indoline-2-one derivative, induces systemic cartilage hyperplasia in rats. *Eur J. Pharmacol.* 418(3):225-30 (2001).

35. F. Demsar, Van Dijke C. F., Kirk B. A., Kapila S., Peterfy C. G., Roberts T. P., Shames D. M., Tomazic S., Mann J., Brasch R. C. Mapping abnormal synovial vascular permeability in temporomandibular joint arthritis in the rabbit using MRI. *Br. J. Rheumatol.* 35(Suppl 3):23-25 (1996).

36. P. B. Jacobson, Morgan S. J., Wilcox D. M., Nguyen P., Ratajczak C. A., Carlson R. P., Harris R. R., Nuss M. A new spin on an old model: in vivo evaluation of disease progression by magnetic resonance imaging with respect to standard inflammatory parameters and histopathology in the adjuvant arthritic rat. *Arthritis Rheum.* 42(10):2060-73 (1999).

37. *The Pharmacological Basis of Therapeutics,* 10$^{th}$ ed, A. Gilman, J. Hardman and L. Limbird, eds., McGraw-Hill Press (2001).

38. *Remington's Pharmaceutical Science's,* 18th ed. Easton: Mack Publishing Co. (1990).

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for treating an inflammatory disease, comprising:
   administering to a subject in need thereof a pharmaceutical composition comprising a N-(2-hydroxypropyl) methacrylamide copolymer and a physiologically acceptable carrier,
   wherein said N-(2-hydroxypropyl) methacrylamide copolymer consists of N-(2-hydroxypropyl) methacrylamide and N-methacryloyl glycylglycyl hydrazone glucocorticoid or a pharmaceutically acceptable salt thereof, and
   wherein said glucocorticoid is dexamethasone.

2. The method of claim 1, wherein the pharmaceutically acceptable salt is dexamethasone palmitate.

3. The method of claim 1, wherein the inflammatory disease is arthritis.

4. The method of claim 3, wherein the arthritis is rheumatoid arthritis.

5. The method of claim 1, wherein the inflammatory disease is selected from the group consisting of tempromandibular joint syndrome, inflamed nerve root, Crohn's disease, chronic obstructive pulmonary disease, psoriasis diseases, asthma, colitis, multiple sclerosis, lupus, erythematosus, and atherosclerosis.

6. The method of claim 1, wherein the subject has an inflamed arthritic joint.

7. The method of claim 6, wherein the joint is an ankle joint.

8. The method of claim 6, wherein the joint is a knee joint.

9. The method of claim 1, wherein the pharmaceutical composition is administered via a route selected from the group consisting of subcutaneous, intravenous, intramuscular, intraperitoneal, intraarticular, and direct local delivery to a site of inflammation.

10. The method of claim 1, wherein the pharmaceutical composition is administered via intravenous delivery.

11. A method for treating rheumatoid arthritis in a human subject, comprising:
    intravenously administering to a subject in need thereof a pharmaceutical composition comprising a N-(2-hydroxypropyl) methacrylamide copolymer and a physiologically acceptable carrier,
    wherein said N-(2-hydroxypropyl) methacrylamide copolymer consists of N-(2-hydroxypropyl) methacrylamide and N-methacryloyl glycylglycyl hydrazone glucocorticoid or a pharmaceutically acceptable salt thereof,
    wherein the glucocorticoid is dexamethasone, and
    wherein the pharmaceutically acceptable salt is dexamethasone palmitate.

* * * * *